US012691224B2

(12) United States Patent
Douglas et al.

(10) Patent No.: US 12,691,224 B2
(45) Date of Patent: *Jul. 28, 2026

(54) DYNAMICALLY CONTROLLED TREATMENT PROTOCOLS FOR AUTONOMOUS TREATMENT SYSTEMS

(71) Applicant: Nextern Innovation, LLC, White Bear Lake, MN (US)

(72) Inventors: Ryan J. Douglas, Seattle, WA (US); Steven M. Gigl, Crystal, MN (US)

(73) Assignee: Nextern Innovation, LLC, White Bear Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,586

(22) Filed: May 14, 2024

(65) Prior Publication Data

US 2025/0114522 A1 Apr. 10, 2025

Related U.S. Application Data

(60) Continuation of application No. 18/183,763, filed on Mar. 14, 2023, now Pat. No. 12,048,832, which is a
(Continued)

(51) Int. Cl.
*A61M 5/172* (2006.01)
*A61H 9/00* (2006.01)
(Continued)

(52) U.S. Cl.
CPC ......... *A61M 5/1723* (2013.01); *A61H 9/0085* (2013.01); *G06Q 10/0639* (2013.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

2011/0264034 A1* 10/2011 Roberts ................. G16H 40/67
604/65
2016/0354039 A1* 12/2016 Soto ........................ A61B 5/74

OTHER PUBLICATIONS

Katuin et al. 2003, "Proton therapy treatment room controls using a Linux control system," Proceedings of the 2003 Particle Accelerator Conference, Portland, OR, USA, 2003, pp. 1068-1070 vol. 2, doi: 10.1109/PAC.2003.1289607.*

(Continued)

*Primary Examiner* — Robert W Morgan
*Assistant Examiner* — Charles P Coleman
(74) *Attorney, Agent, or Firm* — Definitive Patents, member Synchrony IP; Timothy D. Snowden

(57) ABSTRACT

Systems, and methods relate to a medical device receiving a treatment parameter operating point within a first operating region defined by a first set of operating points for which automatic incremental adjustment of a parameter in the current operation is permitted. In an illustrative example, incremental adjustment may use artificial intelligence based on patient feedback and sensor measurement of outcomes. Some exemplary devices may receive a request to alter the current treatment parameter operating point to a second treatment parameter operating point outside the first operating region and in a second operating region in a known safe operation zone, bounded by a known unsafe zone unavailable to the user. In the second operating region, some examples may restrict the step size of incremental adjustments requested by the user. Data may be collected for cloud-based analysis, for example, to facilitate discovery of more effective treatment protocols.

20 Claims, 4 Drawing Sheets

Related U.S. Application Data continuation of application No. 17/007,004, filed on Aug. 31, 2020, now Pat. No. 11,628,253, which is a division of application No. 14/936,462, filed on Nov. 9, 2015, now Pat. No. 10,792,422.

(60) Provisional application No. 62/077,500, filed on Nov. 10, 2014.

(51) Int. Cl.

| | |
|---|---|
| *G06Q 10/0639* | (2023.01) |
| *G06Q 10/10* | (2023.01) |
| *G06Q 50/22* | (2024.01) |
| *G16H 20/10* | (2018.01) |
| *G16H 20/17* | (2018.01) |
| *G16H 20/30* | (2018.01) |
| *G16H 40/40* | (2018.01) |
| *G16H 40/63* | (2018.01) |
| *G16H 40/67* | (2018.01) |
| *G16H 50/20* | (2018.01) |
| *G16H 50/30* | (2018.01) |
| *A61M 1/00* | (2006.01) |
| *A61M 16/00* | (2006.01) |

(52) U.S. Cl.
CPC ............. *G06Q 10/10* (2013.01); *G06Q 50/22* (2013.01); *G16H 20/10* (2018.01); *G16H 20/30* (2018.01); *G16H 40/40* (2018.01); *G16H 40/63* (2018.01); *G16H 40/67* (2018.01); *G16H 50/20* (2018.01); *G16H 50/30* (2018.01); *A61H 9/0092* (2013.01); *A61H 2201/1207* (2013.01); *A61H 2201/1635* (2013.01); *A61H 2201/5005* (2013.01); *A61H 2201/5007* (2013.01); *A61H 2201/5012* (2013.01); *A61H 2201/5043* (2013.01); *A61H 2201/5046* (2013.01); *A61H 2201/5071* (2013.01); *A61H 2201/5089* (2013.01); *A61H 2201/5097* (2013.01); *A61H 2230/00* (2013.01); *A61H 2230/065* (2013.01); *A61H 2230/203* (2013.01); *A61H 2230/208* (2013.01); *A61H 2230/255* (2013.01); *A61H 2230/305* (2013.01); *A61H 2230/505* (2013.01); *A61H 2230/655* (2013.01); *A61M 1/74* (2021.05); *A61M 1/90* (2021.05); *A61M 16/0051* (2013.01); *A61M 2205/3553* (2013.01); *A61M 2205/3561* (2013.01); *A61M 2205/52* (2013.01); *A61M 2230/005* (2013.01); *A61M 2230/06* (2013.01); *A61M 2230/205* (2013.01); *A61M 2230/30* (2013.01); *A61M 2230/50* (2013.01); *G16H 20/17* (2018.01)

(58) Field of Classification Search
CPC ........ G16H 20/13; G16H 20/17; G16H 30/00; G16H 40/00; G16H 50/00; G16H 70/00; G16H 80/00; G16H 20/30; G16H 40/67; G16H 50/30; G16H 50/20; G16H 40/40; G16H 40/63; G06Q 50/22–24; G06Q 10/0639; G06Q 10/10; A61M 5/1723; A61M 1/90; A61M 1/74; A61M 16/0051; A61M 2205/3553; A61M 2205/3561; A61M 2205/52; A61M 2230/005; A61M 2230/06; A61M 2230/205; A61M 2230/30; A61M 2230/50; A61H 9/0085; A61H 9/0092; A61H 2201/1207; A61H 2201/1635; A61H 2201/5005; A61H 2201/5007; A61H 2201/5012; A61H 2201/5043; A61H 2201/5046; A61H 2201/5071; A61H 2201/5089; A61H 2201/5097; A61H 2230/00; A61H 2230/065; A61H 2230/203; A61H 2230/208; A61H 2230/255; A61H 2230/305; A61H 2230/505; A61H 2230/655
USPC .................................................. 705/2, 3, 20
See application file for complete search history.

(56) References Cited

OTHER PUBLICATIONS

Cao et al. 2010, "Secure method for software upgrades for implantable medical devices," in Tsinghua Science and Technology, vol. 15, No. 5, pp. 517-525, Oct. 2010, doi: 10.1016/S1007-0214(10)70095-X.*

* cited by examiner

DYNAMICALLY CONTROLLED TREATMENT PROTOCOLS FOR AUTONOMOUS TREATMENT SYSTEMS

CROSS-REFERENCE TO RELATED APPLICATIONS

This application is a continuation of U.S. application Ser. No. 18/183,763, titled "DYNAMICALLY CONTROLLED TREATMENT PROTOCOLS FOR AUTONOMOUS TREATMENT SYSTEMS," filed by Douglas, et al. on Mar. 14, 2023, which is a continuation of U.S. application Ser. No. 17/007,004, titled "DYNAMICALLY CONTROLLED TREATMENT PROTOCOLS FOR AUTONOMOUS TREATMENT SYSTEMS," filed by Douglas, et al. on Aug. 31, 2020, issued as U.S. Pat. No. 11,628,253, which is a division of U.S. application Ser. No. 14/936,462, titled "DYNAMICALLY CONTROLLED TREATMENT PRO-TOCOLS FOR AUTONOMOUS TREATMENT SYS-TEMS," filed by Douglas, et al. on Nov. 9, 2015, issued as U.S. Pat. No. 10,792,422, and which claims the benefit of U.S. Provisional Application Ser. No. 62/077,500, titled "DYNAMICALLY CONTROLLED TREATMENT PRO-TOCOLS IN CLOSE LOOP AUTONOMOUS TREAT-MENT SYSTEMS," filed by Douglas, et al. on Nov. 10, 2014.

This application incorporates the entire contents of the foregoing applications herein by reference.

TECHNICAL FIELD

Various embodiments relate generally to medical devices, and more specifically to dynamic treatment protocols for optimizing patient outcomes.

BACKGROUND

Advances in personal medical care technology have provided devices useful for unsupervised individual medical treatment. Medical devices that provide therapy on an out-patient, or at-home, basis may supply important healthcare solutions for treating an increasing variety of conditions.

Some out-patient medical devices provide one or more patient monitoring functions. Examples of monitoring functions may include blood pressure monitors, SpO2 blood oxygen sensors, heart rate monitors, or cardiac signature (e.g., ECG). In some systems, electrical impedance mea-surements may be made to measure fluid levels, such as for edema measurements, for example.

Several medical devices for out-patient use offer thera-peutic delivery mechanisms, some of which may be com-bined with monitoring functions. Examples of some thera-peutic delivery systems that may be used by on an out-patient basis may include, for example, insulin pumps, wound care treatment systems, and positive airway pressure systems. Such therapeutic medical devices may be pro-grammed to deliver to the patient a treatment protocol as prescribed by a physician.

SUMMARY

Systems, and methods relate to a medical device receiving a treatment parameter operating point within a first operating region defined by a first set of operating points for which automatic incremental adjustment of a parameter in the current operation is permitted. In an illustrative example, incremental adjustment may use artificial intelligence based on patient feedback and sensor measurement of outcomes. Some exemplary devices may receive a request to alter the current treatment parameter operating point to a second treatment parameter operating point outside the first oper-ating region and in a second operating region in a known safe operation zone, bounded by a known unsafe zone unavailable to the user. In the second operating region, some examples may restrict the step size of incremental adjust-ments requested by the user. Data may be collected for cloud-based analysis, for example, to facilitate discovery of more effective treatment protocols.

Apparatus and associated methods may also relate to sensing the progress and outcomes of medical treatment protocols, interacting with a patient or other users, and automatically adapting treatment protocols for optimal out-comes in response to sensor data and patient feedback. Treatment parameters, such as pressure, temperature, flow, and duration of treatment, which define a treatment protocol, may be automatically varied within safe or approved limits. Treatment parameters beyond safe or approved limits may be denied. Treatment parameters within a safe region but outside of a region for automatically optimized treatment parameter adjustment may be authorized by a patient with consent to collect and share collected data. In an illustrative example, a treatment system may operate to treat a patient's wound with applied pressure while monitoring the patient's blood pressure and heart rate, varying the applied pressure and duration of treatment for optimal healing, while con-straining applied pressure and patient heart rate and blood pressure within safe limits.

Various embodiments may achieve one or more advan-tages. For example, some embodiments may improve effi-ciency of personal medical treatment by allowing more effective therapy automatically customized to a patient's condition and tolerance for treatment. In addition, some embodiments may provide cost savings by allowing patients to avoid regular travel to a clinic for treatment. Some embodiments may improve patient outcomes by automatic adjustment of treatment parameters for optimal therapeutic outcomes. Other embodiments may provide patients with increased autonomy and privacy as they may be able to treat themselves rather than depending on a health care provider for supervised therapy. In addition to the benefits and advantages to the patient, as already described, some embodiments provide an opportunity for society wide improvements to health care therapy, through sensor data and user feedback collected and added to the global knowl-edge base, including the added benefit of the potential for identifying and studying new, more effective medical treat-ment protocols, all while remaining in safe limits.

The details of various embodiments are set forth in the accompanying drawings and the description below. Other features and advantages will be apparent from the descrip-tion and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, the application of a medical care device providing automatic optimization of treatment protocols, according to defined limits and with potential collaboration with a doctor, is introduced in with reference to FIG. 1. Second, with reference to FIG. 2, the discussion turns to exemplary operational scenarios, for a medical care device providing automatic optimization, according to defined limits, of treatment protocols, that illustrate exemplary partitioning of treatment parameter operating points into regions. Specifically, a trajectory of treatment parameter operating points automatically governed by the device as a function of sensor data and user feedback is presented. Third, with reference to FIG. 3, a flow of a process for automatically optimizing treatment parameter operating points, including the decision process invoked to determine if a regional boundary between treatment parameter operating points can be crossed, is presented. Finally, with reference to FIG. 4, the structure of an exemplary medical care device providing automatic optimization of treatment protocols, according to defined limits and with potential collaboration with a doctor, is presented.

Figure 1:
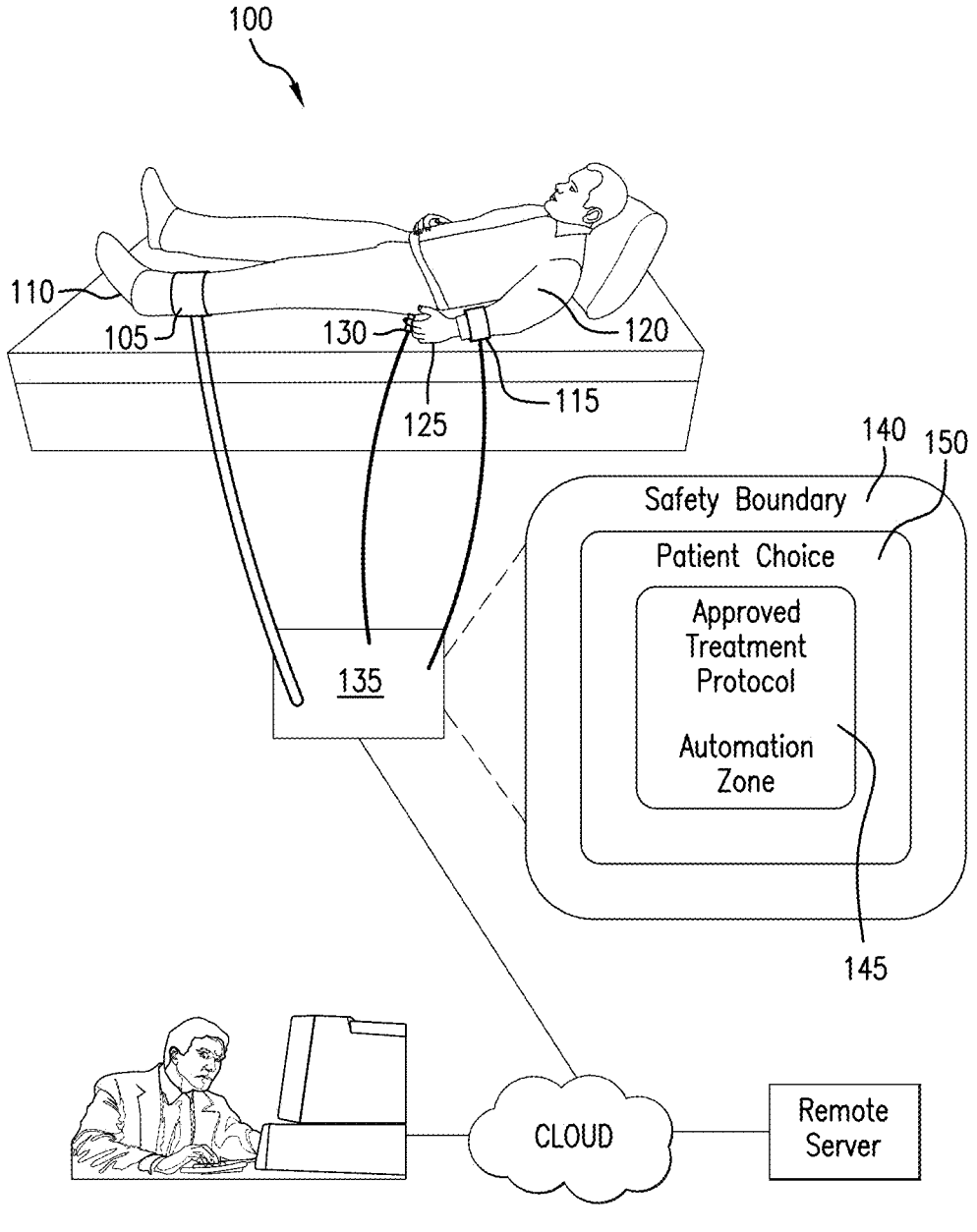
FIG. 1 depicts an exemplary medical care device provid-ing automatic optimization, according to defined limits, of treatment protocols to treat a patient's wound with applied pressure while monitoring the patient's blood pressure and heart rate.

FIG. 1 depicts an exemplary medical care device providing automatic optimization, according to defined limits, of treatment protocols to treat a patient's wound with applied pressure while monitoring the patient's blood pressure and heart rate. In FIG. 1, a patient 100 is wearing an exemplary compression boot 105 attached to patient's leg 110 for treatment of a wound, an exemplary blood pressure measuring cuff 115 attached to patient's arm 120 for monitoring of patient's blood pressure, and an exemplary pulse measurement sensor 125 attached to patient's finger 130 for measurement of patient's heart rate. The compression boot, blood pressure measuring cuff, and pulse measurement sensor are operatively connected with and controlled by treatment system 135 to automatically adjust treatment parameters for optimal care within approved treatment parameter limits. A treatment system defines a set of parameters that define the treatment protocol as a treatment parameter operating point. In an illustrative example, a treatment system partitions the possible treatment parameter operating points into treatment parameter operating point regions 140, including: region 145 designated for automatic adjustment for optimized treatment; region 150 designated for approved treatment parameter ranges driven by a patient with limited increments; and a region circumscribing the region 150 and designated as having unsafe treatment parameter values, for example a request for cuff pressure or treatment duration in excess of a safe limit will not be permitted by a treatment system. In an illustrative example, a treatment system may be communicatively coupled via a cloud connection to a doctor or other health care provider resources.

In an illustrative example, a treatment system may send a request message to a doctor for approval of treatment parameters in various treatment parameter operating point regions, and upon receipt of doctor approval, the treatment system may unlock a broadened set of parameter ranges in the next outer ring of treatment parameter operating point regions. In an illustrative example, a treatment system may allow a doctor at a computer communicatively coupled with a treatment system through a cloud connection to monitor and/or set therapy parameters and update limits in a remote or local server, or in a treatment system, or communicate with a patient directly such as via email, video chat, text message, or other communication capability as would be known to one of ordinary skill in the art.

In an illustrative example, a treatment system may govern a treatment protocol for pressure cuff therapy by measuring, monitoring and controlling treatment parameters including, for example: peak inflation pressure; inflation ramp rate; deflation rate; duration; duty cycle; frequency of treatment; time of day for treatment; location of treatment. These and/or other parameters may form a set of parameters that define the cuff therapy treatment protocol. A particular set of parameters may be referred to herein as a treatment parameter operating point.

In an illustrative example, a treatment system may govern a treatment protocol for insulin pump therapy, by measuring, monitoring and controlling treatment parameters including, for example: bolus volume; flow rate; dispensing duration; times of day; and frequency per day, as a set of parameters that define the insulin pump therapy protocol.

In an illustrative example, the FDA may approve a wound treatment protocol within a range of effective treatment parameters. A wound care treatment may be found to promote healing and minimize swelling between 1.5 LBS of pressure per inch of treatment area and 3 LBS of pressure per inch of treatment area of pressure. The treatment protocol range may then be 2.25+/−0.75 LBS of pressure to the effected region, with corresponding limitations placed on a patient's heart rate and blood pressure during treatment. In an illustrative example, a treatment protocol scenario may begin with treatment parameters including pressure, heart rate, and blood pressure within an FDA-approved operating region, with the compression boot inflated to stimulate circulation and reduce swelling three times per day, while measuring heart rate, blood pressure. The protocol may include getting feedback from the patient about the effectiveness of the treatment, e.g., if pain was reduced, or numbness became apparent.

Based on feedback sensor data and/or patient feedback, the treatment parameters may be adapted, by an artificial intelligence (AI) application associated with the treatment system. In some implementations, the AI application may be partially or wholly executed on the remote or local server or database. The AI application may cause the treatment system 135 to adjust its operating point parameters in an on-going treatment or in future treatments. In an illustrative example, the AI may determine to incrementally increase or decrease the peak cuff compression pressure. In another example, the AI application may determine to incrementally adjust a frequency or interval between treatments. The adjustments made by the AI application may be restricted to predetermined increments, which may be within limits approved by FDA, and/or authorized by a doctor's orders.

In an illustrative example, a treatment system may adjust treatment parameters to optimize treatment as a function of feedback on patient outcomes from sensor data measured and analyzed by a treatment system. In an illustrative example, sensor data used by a treatment system for feedback on patient outcomes may include patient body temperature or applied treatment temperature, applied treatment pressure, patient heart rate, patient blood oxygen (SPO2) level, or patient blood pressure. In addition, sensor data from common exercise or fitness monitors, including wrist worn activity monitors, may be collected for feedback on patient outcomes. Data from various sensors and input devices may be collected by the treatment system 135, for example. Various data sources may connect to the treatment system 135 via wired or wireless links. In some implementations, data may be delivered to the remote or local server, which may receive data collected by the treatment system 135. In some examples, data may be downloaded from the remote or local server to the treatment system 135 for processing locally at the patient's site.

In an illustrative example, sensor data representative of patient heart rate, blood oxygen level, and blood pressure may define a treatment parameter operating point below an optimal treatment parameter operating point for a certain treatment protocol. Based on the sensor data, a treatment parameter, such as an applied treatment temperature or pressure for example, may be increased for optimal therapeutic outcome for the particular patient, while maintaining heart rate, blood pressure, and blood oxygen within approved, safe limits.

In an illustrative example, a treatment system may adjust treatment parameters to optimize treatment as a function of feedback on patient outcomes from patient survey data obtained by a treatment system. In an illustrative example, a treatment system may poll a user, and collect, and analyze user responses. In an illustrative example, patient survey data used by a treatment system for feedback on patient outcomes may include: responses to questions from the treatment system such as asking a patient how they feel; rating their pain on scale of 1-10; asking if a treatment protocol or parameter relieved pain, or increased pain; or asking if numbness or tingling increased, decreased, appeared, or disappeared. In addition, a treatment system may collect and analyze user response to questions about patient activities and daily performance including the duration and quality of sleep, exercise levels, food intake, allergies, medications, fluid intake, smoking, and so on. In an illustrative example, in view of a recent intake of caffeine as determined by a patient survey, a treatment system may adapt treatment parameters for a treatment protocol by adjusting blood pressure allowed during treatment.

In an illustrative example, a treatment system may adjust treatment parameters to optimize treatment as a function of feedback on patient outcomes from health care provider survey data. In an illustrative example, a treatment system may interrogate health care providers, collect, and analyze health care provider response. In an illustrative example, health care provider survey data used by a treatment system for feedback on patient outcomes may include: responses to questions from a treatment system via electronic communication to ask relevant questions via electronic communication of nurses, pharmacists, physicians, nutritionists, and so on. In an illustrative example, a treatment system may determine from a patient survey that a patient has not taken their blood pressure medication, and the same treatment system may learn from inquiring of the patient's doctor via electronic communication that in view of these conditions, a safe blood pressure parameter limitation should be enforced for a scheduled treatment.

Figure 2:
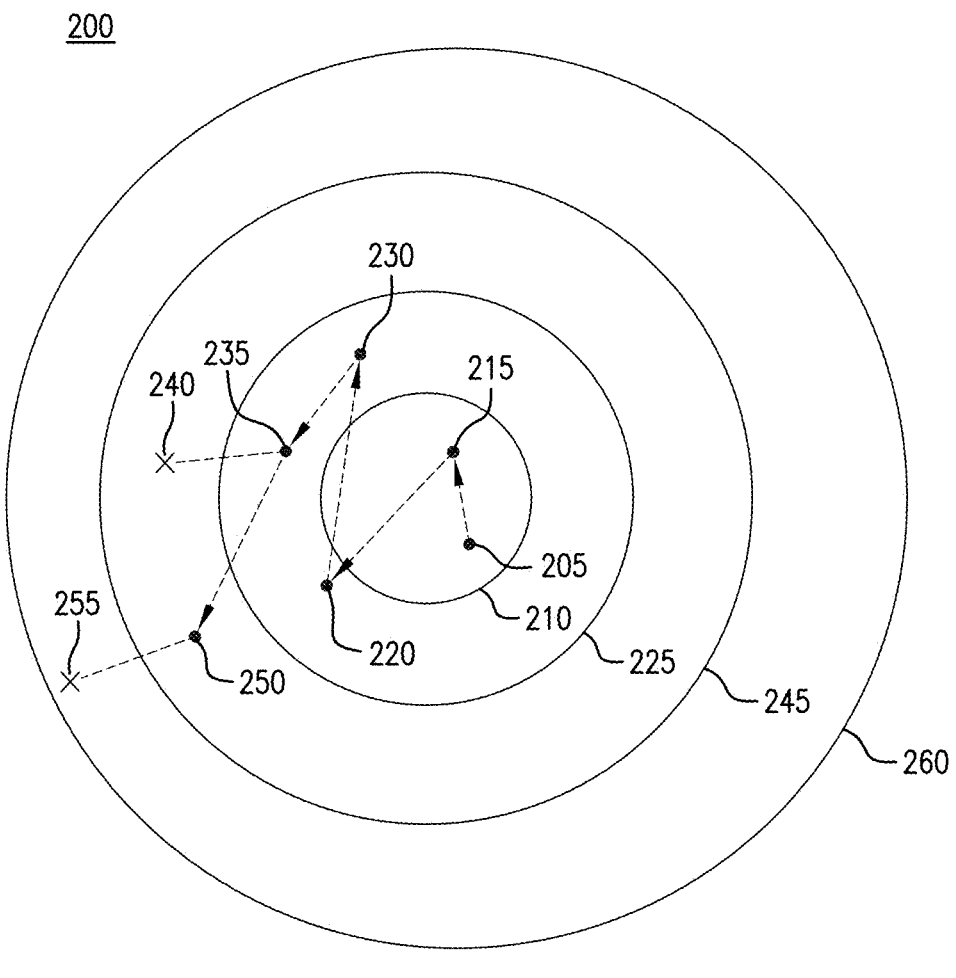
FIG. 2 depicts a detail view of an exemplary partitioning of treatment protocol operating points into regions including personalized treatment, automatic treatment, patient autho-rized treatment, and safety limited zones.

FIG. 2 depicts a detail view of an exemplary partitioning of treatment protocol operating points into regions including personalized treatment, automatic treatment, patient authorized treatment, and safety limited zones. In FIG. 2, a partitioning 200 into regions or zones of treatment parameter operating points is illustrated.

By way of example and not limitation, a treatment parameter operating point may represent a combination of treatment parameters including pressure, frequency, heart rate, respiration rate, flow rate, treatment frequency, treatment schedule, time of treatment, or other measured or effected treatment parameters known to one of ordinary skill in the art.

A treatment protocol scenario may begin with a treatment parameter operating point 205 located with treatment parameters personalized or customized by a user to values within an approved, safe treatment parameter operation point region 210 designated for user-customized, or personalized, treatment. In some implementations, the treatment system may be programmed to give the patient discretion to adjust the operating point to a new treatment parameter operating point 215 that is within the region 210. This limited operating region 210 may provide for minor, unsupervised adjustments that deviate from the initial operating point prescribed by the physician, for example.

In response to feedback including sensor data or user response, a treatment system may automatically adjust treatment parameters within approved limits to a new treatment parameter operating point 220, within a region 225 designated for automatic adjustment of treatment parameters within approved limits. In an illustrative example, a treatment scenario may continue with automatic adjustment, under a closed-loop automatic control and/or responsive to an AI engine configured to automatically adjust the operating point on a search to find an optimal patient outcome. In this region 225, the treatment system may automatically adjust the operating point in response to sensor monitoring and patient feedback. Using incremental adjustment of parameters, the treatment system may incrementally move the operating point of parameters along a trajectory within the region 225 to seek a treatment parameter operating point 230 that produces optimal patient health outcomes. Accordingly, the operating point of parameters may be automatically migrated within the treatment parameter region 225 approved for automatic treatment. In some embodiments, the operating point under AI control may migrate anywhere within the regions 210, 225.

In an illustrative example, a treatment scenario may continue with automatic adjustment in response to monitoring and feedback, and a new treatment parameter operating point 235 may be automatically selected within the treatment parameter region 225 approved for automatic treatment.

In an illustrative example, a patient may select treatment parameters at a treatment parameter operating point 240 located outside the boundary of the region 225, and in a region 245 designated for treatment parameter values requiring boundary authorization. Upon encountering this boundary between the regions 225, 245, a treatment evaluation and boundary authorization procedure is invoked. In this example, authorization to cross the boundary from the region 225 into the region 245 is not obtained, and treatment remains at the treatment parameter operating point 235 within the region 225.

The patient may then select treatment parameters at a treatment parameter operating point 250 located outside the boundary of the region 225, and in the region 245 designated for treatment parameter values requiring boundary authorization. In response to this attempt to expand the treatment protocol operating point into the region 245, a treatment evaluation and boundary authorization procedure is invoked.

If authorization is obtained, such as from a physician, then treatment continues at the new treatment parameter operating point 250.

Within the region 245, the treatment system may govern the maximum increment or step size of any parameter changes. For example, for operating points within the region 245, the patient can self-direct changes to the therapy, but may only change parameters between sessions or within an on-going session within predetermined limits programmed by the physician and/or device manufacturer. The degree or amplitude of the parameter changes may be limited by a governor function of the device. These limits or parameter governor functions may advantageously protect the patient from radically altering the therapy in an uncontrolled way that is very different from recent, familiar operating points. This may advantageously protect the patient from receiving an erratic course of therapies that may reduce the diagnostic value of the feedback on patient outcomes. In some examples, the treatment system may only permit changes to one parameter at a time. In some examples, the treatment system may impose minimum dwell times on some operating points, to allow the patient's body time to respond to an operating point before the patient is allowed to change that parameter. For example, the treatment system may only allow the patient to increase the duration of a therapy by 5 minutes, with a minimum dwell time of 1 week; accordingly, the treatment system would not allow the patient to increase the duration again until the previous increase had been in place for at least 1 week. In some embodiments, the treatment system may not impose a dwell time requirement to revert to a prior operating point, such as the operating point 235. This may advantageously allow a patient to test a new operating point, but still prevent unintended stress on the patient when the patient instructs the treatment system to rapidly alter a therapy to unfamiliar operating points to which the patient is not accustomed.

In an illustrative example, a patient may select treatment parameters to transition from the operating point 250 to a treatment parameter operating point 255 located within a region 260. In various embodiments, the maximum safe operating area for therapeutic use of the device may be circumscribed by the outer limit of the region 260.

Parameter configurations that extend outside of the region 260 are designated as unsafe for treatment. Such operating points may be disallowed by hardware and or software of the treatment system. Patient selection of an unsafe treatment parameter operating point is automatically denied, with treatment continuing at the previous treatment parameter operating point within any of permissible or safe regions 310, 225, 245, 260. In some embodiments, the treatment system may send an electronic message or alert upon a boundary crossing from an interior region to an exterior region, for example. In some examples, a physician may be alerted (e.g., by email, SMS text message, phone call) upon an attempt by the patient to expand the treatment protocol range by entering the region 245 or 260. In some examples, the device manufacturer may be alerted if the patient attempts to move the operating point outside of the maximum safe operating area circumscribed by the outer limit of the region 260.

In some embodiments, the treatment system may receive upgrades to software from the remote or local server. The server may update the parameter ranges associated with each of the regions 210, 225, 245, 260, for example, to reflect new knowledge of safe operating regions, best practices, and/or optimal treatment protocols. The physician may alter the shape or size of the region 245, for example, based on new knowledge about the specific patient, changes in best protocol practices, or as a function of the patient's physical age, health status, or preferences, for example.

Figure 3:
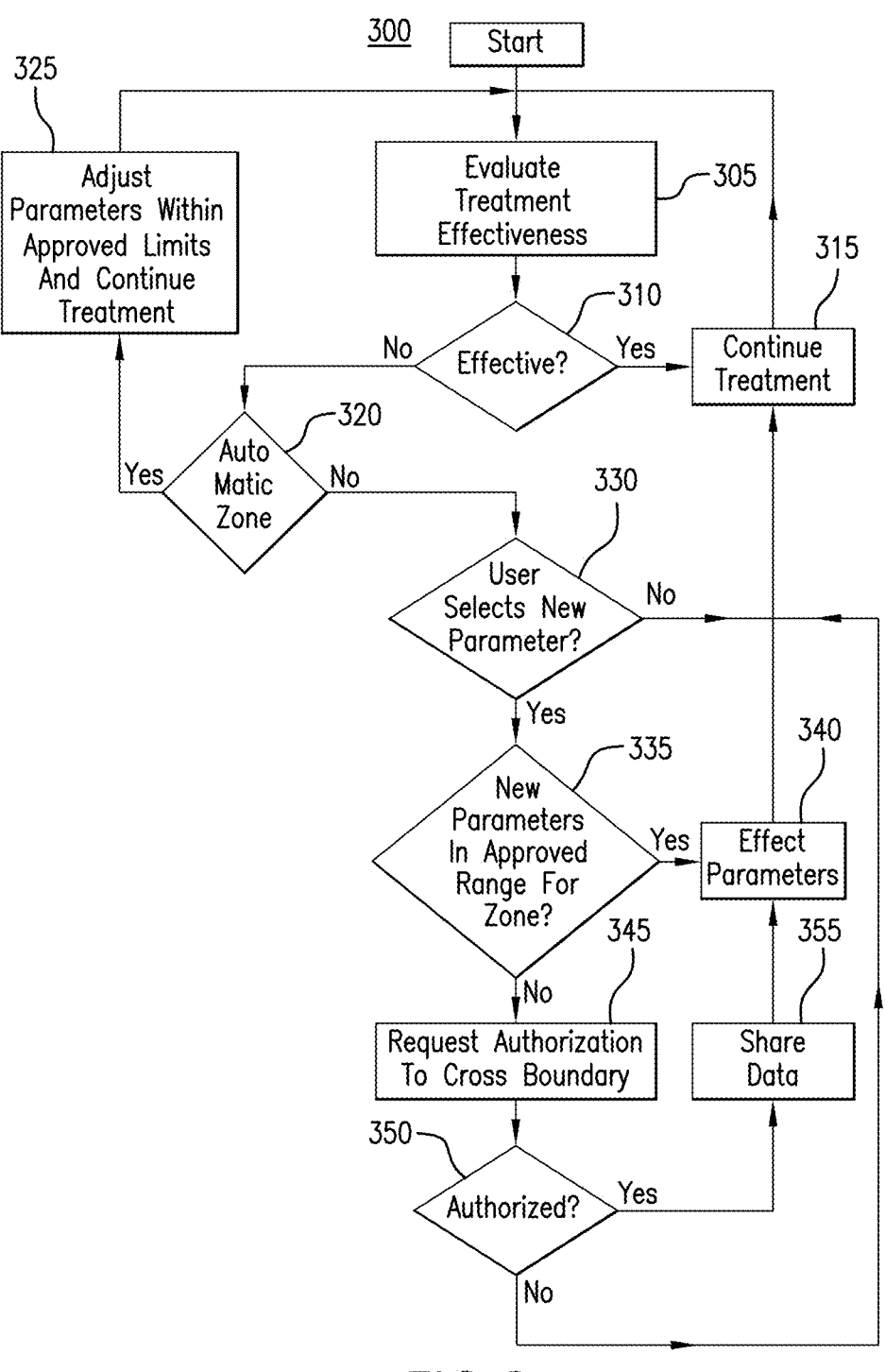
FIG. 3 depicts an operational flow of an exemplary medical care device providing automatic optimization with reference to defined limits of a treatment protocol.

FIG. 3 depicts an operational flow of an exemplary medical care device providing automatic optimization with reference to defined limits of a treatment protocol. In FIG. 3, a computer-implemented method 300 is disclosed for automatic treatment parameter operating point adjustment including treatment evaluation and boundary authorization. In a first stage, at step 305, treatment effectiveness is evaluated as a function of sensor data, expected results from treatment protocols, user feedback, or historical data. In a second stage, at step 310, a test is performed to determine if treatment was effective. If the treatment is effective, at step 315, then treatment continues with the treatment parameter operation point unchanged, and the method returns to step 305 at a later time. If the treatment is not effective, at step 320, then a test is performed to determine if operational treatment parameters are within a zone designated for automatic treatment parameter adjustment. An example of such a zone is described with reference to the region 225 of FIG. 2.

If operational treatment parameters are within a zone designated for automatic treatment parameter adjustment, then, at step 325, operational treatment parameters are incrementally adjusted within approved limits, and treatment continues with a new treatment parameter operating point, with the method returning to step 305 at a later time.

If operational treatment parameters are not within a zone designated for automatic treatment parameter adjustment, then, at step 330, a test is performed to determine if a user has selected new treatment parameters. If a user has not selected new treatment parameters, then treatment continues to step 315 with the treatment parameter operation point unchanged.

If a user has selected new treatment parameters, then, at step 335, a test is performed to determine if the new parameters are within an approved range. If the new parameters are within an approved range, then, at step 340, the new parameters are put into effect, and treatment continues with a new treatment parameter operation point, and the method returns to step 315.

If the new parameters are not within an approved range, then, at step 345, warnings are issued to the user, authorization is requested to cross the treatment parameter operation point boundary to a region requiring authorization, and authorization to share user and sensor data is requested. At step 350, a test is performed to determine if a user has authorized crossing the treatment parameter operation point boundary to a region requiring authorization, and to share user and sensor data. If the user has authorized crossing the treatment parameter operation point boundary to a region requiring authorization, and to share user and sensor data, then, at step 355, data is shared and the new parameters are put into effect at step 340. Upon a determination a user has not authorized crossing the treatment parameter operation point boundary to a region requiring authorization, and to share user and sensor data, treatment continues with the treatment parameter operation point unchanged at step 315.

Figure 4:
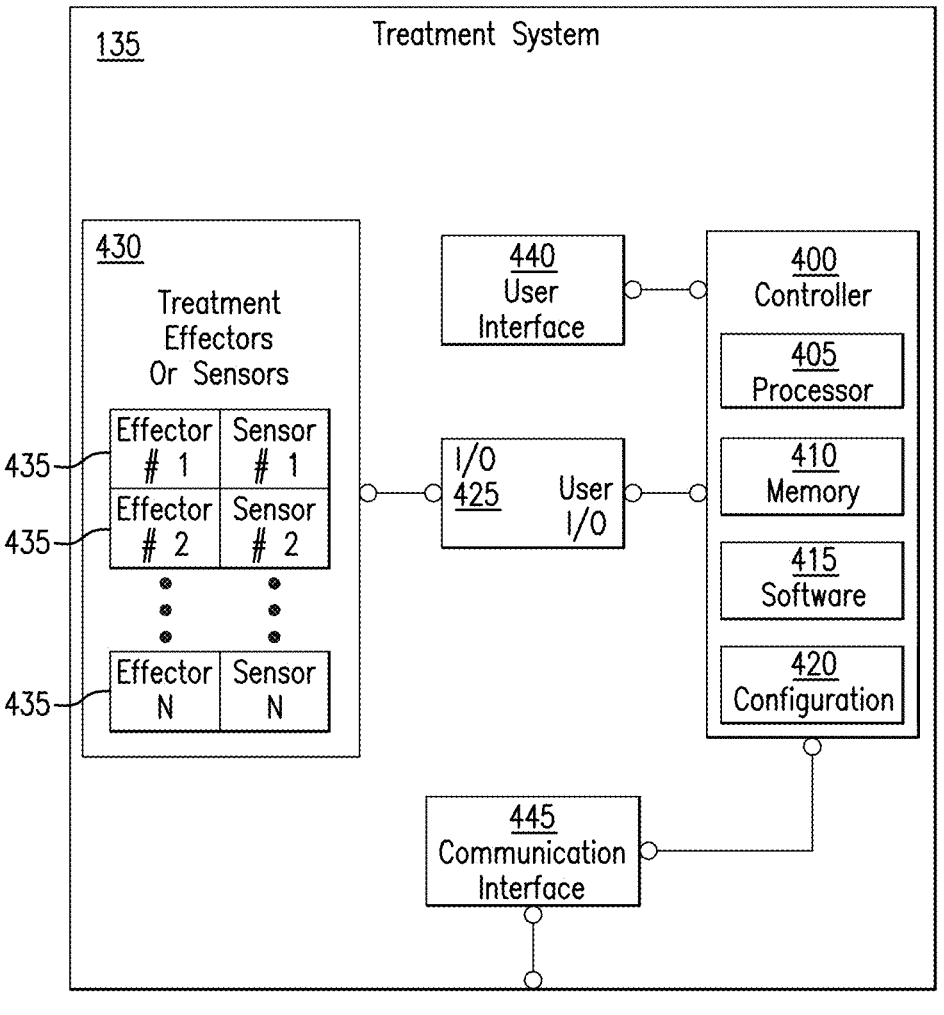
FIG. 4 depicts the structure of an exemplary medical care device providing automatic optimization, according to defined limits, of treatment protocols.

FIG. 4 depicts the structure of an exemplary medical care device providing automatic optimization, according to defined limits, of treatment protocols. As illustrated in FIG. 4, a treatment system 135 of FIG. 1 includes a controller 400 having a processor 405, a memory 410, software 415, and configuration 420 operative to control treatment according to regions of treatment protocol operating points. Examples of such regions were described with reference to FIG. 2, for example. The controller 400 is operatively coupled via Input/Output System 425 to Treatment Effectors Module 430 which may comprise a plurality of types and configurations of Treatment Effectors or Sensors 435. In an illustrative example, the Treatment Effectors or Sensors 435 may include inflatable compression boots or cuffs, blood pressure sensors, pumps such as an insulin pump, pulse rate sensors, gas composition sensors such as an Oxygen sensor, liquid composition sensors such as a blood glucose sensor, temperature sensors, or other sensors or effectors known to one of ordinary skill in the art. In an illustrative example, a treatment system may solicit user response or process or user direction received through User Interface 440. In an illustrative example, Communication Interface 445 communicatively couples the treatment system with remote resources including servers, databases, doctors, or other caregivers.

Although various embodiments have been described with reference to the Figures, other embodiments are possible. For example, various embodiments may improve patient safety, product efficacy, and facilitate FDA approval. In particular, one goal of dynamic treatment control may be to position a device manufacturer to aggregate clinically significant, anonymous, and/or stratified by user profile data around how a population of patients use a therapeutic medical device. The aggregated data may facilitate improved, faster, or perhaps real-time updating of the standard of care for a specific disease. Some treatments may be analyzed, for example, in real-time. This may dramatically improve the database for effective therapeutic protocols that can be used to provide new insights into effectiveness of treatment protocol using current approved and/or off-label, patient directed therapies conducted within safe limits. In some treatments that can be automated, substantially real-time updates may provide the knowledge to update the treatment protocols in real-time, to shift to the latest standard of care, and further personalize treatment based on "as it happens" user sensing and input.

Although existing medical treatment systems can be effective, a user may need to carefully follow treatment parameters as instructed by a doctor. Treatment parameters which a user may need to carefully adjust, monitor, or control during the course of treatment may include pressure, temperature, duration of treatment, in addition to recording the outcome of treatment, for example, whether a treatment seemed to improve the patient's condition, or if increased pressure or duration helped reduce swelling. Various embodiments may provide an improved treatment system capable of sensing the progress and outcomes of treatment protocols, interacting with and interfacing with the patient or other users, and automatically adapting treatment protocols for optimal patient therapeutic or health outcomes.

The FDA may not immediately approve any medical device that will dynamically shift the treatment protocol without human intervention, monitoring and approval. However, the goal is to develop systems that are responsive both to the patient and the current state of the art. In this way, the goals of the device manufacturer and the goals of the regulators may not be aligned.

In some embodiments, the systems described herein may be designed to provide maximum personalized medical treatment while staying within a treatment regime that can be readily verified and validated to meet FDA's regulatory requirements.

The over-arching concept is to provide "controlled flexibility," allowing the system to dynamically adjust treatment protocols within a specified, pre-tested, parameter range that is comfortable for the regulators. Use outside the specified ranges, like any off-label use, would be at the discretion of the patient and their chosen medical professional. The system would alert the user they have select parameters outside the approved treatment protocol. The user would need to knowingly consent to change the treatment outside the approved protocol either by making a treatment parameter change or by altering their use of the system, such as frequency or duration of use. If they choose to do so they would be asked to donate their data for study. The system would monitor their progress, grouping like patients together and monitoring the effects of the modified treatment protocol. Data including user feedback, sensor data, and treatment outcomes from user treatment experiences may be collected and aggregated as server statistics, and the data collected can be analyzed, depersonalized, and used to educate health care workers, and identify more effective treatment protocols.

Once enough data is gathered the results would be presented to the FDA. Approval to widen treatment parameters or alter the intended use of the product would be requested of the FDA. If granted, the system would be updated to include the new treatment protocol or indications for use as part of the standard of care, thereby broadening the area of controlled flexibility that may be offered to the patient population. If such approval was not granted solely on the basis of the data collected, the data could be used to help design a more traditional study and gain approval by the FDA to conduct such a study.

Once the treatment protocol "tolerances" are opened, each user who had previously been using the system (prior to update) would be alerted and would need to opt-in to have their device updated. Once opted-in the patient would benefit from a greater range of automated treatment solutions, but would only receive a new treatment if their individual needs matched the profile for the newer treatment regime.

In some embodiments, the concept may be achieved by the following steps.

Step 1: Prior to automation, manual clinical trials may be conducted to establish the efficacious boundaries (tolerance) of the treatment protocol. Specifically, for example, the dose and/or treatment may be tested to the edges of diminishing effect and/or unacceptable side-effects to establish the boundaries of clinical effectiveness.

Step 2: The FDA may evaluate the treatment protocol in the broadest range that may have been found to provide clinically significant treatment results. The FDA may then approve the treatment protocol within the range of effective treatment. For example, a wound care device may be found to promote healing and minimize swelling between 1.5 LBS of pressure per sq. inch of treatment area and 3 LBS of pressure per sq. inch of treatment area. The treatment protocol range may then be 2.25+/−0.75 LBS of pressure to the effected region.

Step 3: The system may then set the autonomous treatment parameters to match the FDA approval. 2.25+/−0.75 LBS per sq. inch of pressure within the range of the FDA approved treatment protocol.

Step 4: The system may use a combination of standard of care data, (updated by most recent studies and by patient population use), individual data (sensed and solicited) to adjust individual treatment protocols within the allowed treatment protocol.

Step 5: Individual treatment protocol may not be adjusted automatically beyond FDA evaluated tolerances.

Step 6: To help ensure compliance and manage risk, if the user moves outside the established and FDA approved treatment protocol the individual user may be notified that they are operating the device outside of known clinical applications.

Step 7: When required, control boundaries may be in place that only allow the treatment protocol to be modified marginally outside the approved treatment parameters' zone of operation, and may prevent operation for known unsafe parameters.

Step 8: New treatment protocols may be developed and tested outside of the FDA approved treatment protocol. The new treatment protocols may be still within controlled limits with may require informed consent of the user.

Step 9: All users who have elected to make their data available for study and who may operate outside the FDA approved protocol may be monitored and their data may be analyzed. If these users experience degradation in health or care, then the protocol may be discontinued and may be made not available to additional users. The treatment algorithm may then be altered accordingly.

Step 10: If the protocol is determined (measured) to be effective, but outside the FDA approved treatment protocol, the device manufacturer may be alerted of a new potential universal treatment protocol.

Step 11: The device manufacturer may internally evaluate the new universal treatment protocol per FDA guidance for resubmission of devices.

Step 12: If the treatment protocol is found to be within the allowable adjustments to the device treatment protocol without additional FDA approval, device manufacturer may update the outside boundaries of the autonomous adjusting treatment protocol system. A manual update (e.g., an update made by a human) may be made to the total treatment tolerance and the system may be permitted to extend a broader treatment protocol to the patient population. Go to step 17.

Step 13: If the new treatment protocol is found to be outside the allowable treatments (without further FDA evaluation) the device manufacturer may contact the FDA and may obtain approval to further study the new treatment protocol. During this time the universal treatment protocols may not be updated and the same treatment constraints for the greater user population may be maintained.

Step 14: Additional studies may be conducted, perhaps by monitoring the patient population who has knowingly chosen to operate outside the FDA approved treatment protocols.

Step 15: Once a statistically significant amount of treatment effectiveness data is collected, the findings may be submitted to the FDA.

Step 16: If the FDA accepts a finding that the tolerances of the universal treatment protocol or changes to the intended use of the product are updated with greater flexibility and may be made available to the entire population through automated (dynamic) updating of the treatment protocol based on patient need, preference and ultimately effective and quantified treatment.

Step 17: Patients may be alerted that broader treatment protocols or new treatments are available and may be asked if they wish to opt-in for the new treatment protocols. If they elect to opt-in the new treatments may be made available to them. These new treatments may be only utilized if the patient profile matches the parameters for these new treatment protocols.

Step 18: In cases where the updates to the treatment protocol are to ensure patient safety or adjust a treatment protocol with the latest information (e.g., narrowing the treatment parameters). A patient's treatment protocols may be altered and some patients may be required to opt-in. If they do not opt-in, the device may not function outside the new safety parameters and the patient may be asked to contact the company or their physician.

Step 19: Once new safety boundaries are in place, the patient may receive specific warnings if they attempt to use the device outside the known safety limits. In some cases the device may not permit use outside the specific safety boundaries.

Step 20: New universal treatment protocols and/or broadened indications for use may be made available to the system. Tolerances may be updated to match the latest treatment. Go to step 4.

In some embodiments, a method of dynamically altering treatment methods may be performed by a computer system. For example, a medical device may communicate with a cloud based server. In some embodiments, the cloud based server may act as a SAAS (software as a service) model and/or interface with remote servers in a license/seat model. A decision engine may operate remotely in some embodiments. In an exemplary embodiment a decision engine may operate locally (e.g., a decision engine may be included in the medical device). A neural network or other machine learning algorithm may be accessible to the decision engine.

In some embodiments, a medical device may communicate with the cloud via a wireless interface. In some embodiments, an APP for a mobile device may interface with a cloud based server. In an exemplary embodiment the APP may communicate with the medical device. In this way, the APP could serve as an intermediary between the cloud based server and the medical device. In an exemplary embodiment, an APP template may be provided to medical device manufacturers to facilitate dynamic treatment behaviors for medical devices that these manufacturers develop.

Some embodiments may be in the form of a method of treatment. In some embodiments, software may facilitate the FDA approval process. In an exemplary embodiment, software may facilitate the physician to remotely adjust a treatment protocol for a patient. Medical device companies may use data from remote users to facilitate development of new treatment protocols.

Some aspects of embodiments may be implemented as a computer system. For example, various implementations may include digital and/or analog circuitry, computer hardware, other sensors (e.g., temperature sensors, impedance sensors, pressure sensors), firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer. For example, wearable devices, such as augmented reality systems or other technologies may facilitate input and/or output operations between a user and a system.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g/n/ac, Wi-Fi, LTE, Bluetooth, BLE, ZigBee, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

Apparatus, systems, and methods useful for personal medical care in contexts including home health care are disclosed. Various embodiments may be equipped to sense the progress and outcomes of treatment protocols, interact with and interface to the patient or other users, and automatically adapt treatment protocols for optimal outcomes, by automatically varying, with reference to defined limitations, treatment parameters such as pressure, temperature, length of treatment, or treatment schedule, in response to monitored sensor data, patient response, or doctor authorization. Data may be collected for cloud-based analysis or decision, to drive the discovery of more effective treatment protocols.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated, within the scope of the following claims.

What is claimed is:

1. A therapeutic delivery method comprising:
   providing a therapy delivery mechanism operably coupled to a processor and adapted to deliver a therapy to a patient according to a treatment parameter operating point defined by a set of parameters associated with the delivery of the therapy in response to receiving a command signal transmitted by the processor;
   providing a communication interface configured for communicating information about the patient to a remote or local server, the communicated information including information about a result of the therapy applied to the patient by the therapy delivery mechanism;
   providing the processor operably coupled to control the therapy delivery mechanism according to the treatment parameter operating point, and operably coupled to the communication interface to generate a message that includes the result of the therapy applied to the patient by the therapy delivery mechanism; and,
   providing a memory device operably coupled to the processor and containing instructions, that when executed by the processor, cause the processor to perform operations to dynamically adjust the treatment parameter operating point, the operations comprising:
      request authorization to alter the treatment parameter operating point from a first predetermined operating region defined by a first set of operating points for which automatic incremental adjustment of a parameter in the current operation is permitted to a second predetermined operating region that lies outside of the first predetermined operating region in a space of operating points;
      if the requested authorization is received, then generate a second command signal to the therapy delivery mechanism for delivering therapy to the patient according to the second treatment parameter operating point; and, if the requested authorization is denied, then generate a first command signal to the therapy delivery mechanism for delivering therapy to the patient according to the first treatment parameter operating point.

2. The method of claim 1, wherein the operations further comprise: generate a message to send to the remote or local server via the communication interface, said message containing data about the therapy applied to the patient by the therapy delivery mechanism.

3. The method of claim 1, wherein the operations further comprise:

while the current operating point is in the first predetermined operating region, calculate an incrementally different treatment parameter operating point based on a function of at least one sensor measurement of the patient and a survey of user responses; and while the current operating point is in the second predetermined operating region, calculating a maximum allowed increment for the patient to adjust a parameter of the treatment parameter operating point.

4. The method of claim 1, wherein the predetermined therapy comprises insulin therapy, and the therapy delivery mechanism comprises an insulin pump.

5. The method of claim 1, wherein the predetermined therapy comprises wound care treatment.

6. The method of claim 1, wherein the predetermined therapy is positive airway pressure therapy.

7. The therapeutic delivery method of claim 1, wherein the operations further comprise, receive the current treatment parameter operating point that lies within the first predetermined operating region.

8. The therapeutic delivery method of claim 1, wherein the operations further comprise, receive a request to alter the current treatment parameter operating point to a second treatment parameter operating point that lies outside of the first predetermined operating region and in a second predetermined operating region defined by the second set of operating points for which authorization is required.

9. The therapeutic delivery method of claim 1, wherein the operations further comprise:

adapting the therapy delivery mechanism to deliver a first predetermined therapy to the patient in response to the first command signal being received at the therapy delivery mechanism, wherein the first predetermined therapy is associated with the first treatment parameter operating point, and, adapting the therapy delivery mechanism to deliver a second predetermined therapy to the patient in response to the second command signal being received at the therapy delivery mechanism, wherein the second predetermined therapy is associated with the first treatment parameter operating point.

10. A therapeutic delivery apparatus comprising:

a communication interface configured for communicating information about the patient to a remote or local server, the communicated information including information about a result of a therapy applied to a patient by a therapy delivery mechanism operably coupled to a processor, wherein the therapy delivery mechanism is adapted to deliver the therapy to the patient according to a treatment parameter operating point defined by a set of parameters associated with the delivery of the therapy;

the processor operably configured to control the therapy delivery mechanism according to the treatment parameter operating point, and operably coupled to the communication interface to generate a message that includes the result of the therapy applied to the patient by the therapy delivery mechanism; and, a memory device operably coupled to the processor and containing instructions, that when executed by the processor, cause the processor to perform operations to dynamically adjust the treatment parameter operating point, the operations comprising:

request authorization to alter the treatment parameter operating point from a first predetermined operating region defined by a first set of operating points for which automatic incremental adjustment of a parameter in the current operation is permitted to second predetermined operating region that lies outside of the first predetermined operating region in a space of operating points;

if the requested authorization is received, then generate a second command signal to the therapy delivery mechanism for delivering therapy to the patient according to the second treatment parameter operating point, wherein in response to the second command signal being received at the therapy delivery mechanism, the therapy delivery mechanism delivers a second therapy to the patient, the second therapy being associated with the second treatment parameter operating point.

11. The apparatus of claim 10, wherein the operations further comprise: generate a message to send to the remote or local server via the communication interface, said message containing data about the therapy applied to the patient by the therapy delivery mechanism.

12. The apparatus of claim 10, wherein the therapy comprises insulin therapy, and the therapy delivery mechanism comprises an insulin pump.

13. The apparatus of claim 10, wherein the therapy comprises wound care treatment.

14. The apparatus of claim 10, wherein the therapy is positive airway pressure therapy.

15. The apparatus of claim 10, wherein the operations further comprise: generate a message to send to the remote or local server via the communication interface, said message containing data about at least one of: the therapy applied to the patient by the therapy delivery mechanism, and the result thereof.

16. The apparatus of claim 10, wherein the communication interface is further configured for receiving information about a first range of parameters that define the first predetermined operating region, and for receiving information about a second range of parameters that define the second predetermined operating region.

17. The apparatus of claim 10, further comprising a user interface coupled to the processor and configured to receive user input representing user feedback about the result of the therapy applied to the patient by the therapy delivery mechanism.

18. The apparatus of claim 10, wherein the operations further comprise: generate a message to send to the remote or local server via the communication interface, said message containing data about sensor measurements and user input feedback associated with the therapy applied to the patient by the therapy delivery mechanism.

19. The apparatus of claim 10, wherein the operations further comprise, while the current treatment parameter operating point is in the first predetermined operating region, calculating an incrementally different treatment operating point based on a function of at least one sensor measurement of the patient and a survey of user responses, and while the current treatment parameter operating point is in the second predetermined operating region, calculating a maximum allowed increment for the patient to adjust a parameter of the treatment parameter operating point.

20. The apparatus of claim 10, wherein the operations further comprise, if the requested authorization is denied, then generate a first command signal to the therapy delivery mechanism for delivering therapy to the patient according to the first treatment parameter operating point, wherein:

in response to the first command signal being received at the therapy delivery mechanism, the therapy delivery mechanism delivers a first predetermined therapy to the patient, the first predetermined therapy being associated with the first treatment parameter operating point.

\* \* \* \* \*